US010045752B2

United States Patent
Gupta et al.

(10) Patent No.: US 10,045,752 B2
(45) Date of Patent: Aug. 14, 2018

(54) METHOD FOR CODED-SOURCE PHASE CONTRAST X-RAY IMAGING

(71) Applicants: Rajiv Gupta, Wayland, MA (US); Luis Fernando Velasquez-Garcia, Cambridge, MA (US); Richard Lanza, Cambridge, MA (US); Berthold K P Horn, Boston, MA (US); Akintunde Ibitayo Akinwande, Cambridge, MA (US)

(72) Inventors: Rajiv Gupta, Wayland, MA (US); Luis Fernando Velasquez-Garcia, Cambridge, MA (US); Richard Lanza, Cambridge, MA (US); Berthold K P Horn, Boston, MA (US); Akintunde Ibitayo Akinwande, Cambridge, MA (US)

(73) Assignees: The General Hospital Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 117 days.

(21) Appl. No.: 14/400,703

(22) PCT Filed: Mar. 14, 2013

(86) PCT No.: PCT/US2013/031602
§ 371 (c)(1),
(2) Date: Nov. 12, 2014

(87) PCT Pub. No.: WO2013/187970
PCT Pub. Date: Dec. 19, 2013

(65) Prior Publication Data
US 2015/0146848 A1    May 28, 2015

Related U.S. Application Data

(60) Provisional application No. 61/646,577, filed on May 14, 2012.

(51) Int. Cl.
*A61B 6/00* (2006.01)
*G01N 23/04* (2006.01)
(Continued)

(52) U.S. Cl.
CPC ............... *A61B 6/484* (2013.01); *A61B 6/40* (2013.01); *A61B 6/405* (2013.01); *A61B 6/4007* (2013.01);
(Continued)

(58) Field of Classification Search
CPC ......... A61B 6/40; A61B 6/4007; A61B 6/405; A61B 6/484; G01N 23/04; G01V 5/0016
(Continued)

(56) References Cited

U.S. PATENT DOCUMENTS 3,936,639 A * 2/1976 Barrett .................... G01T 1/295
250/366
4,078,177 A * 3/1978 Tiemens ................ A61B 6/025
359/24
(Continued)

FOREIGN PATENT DOCUMENTS

WO     2012/032950 A1    3/2012
WO     2012056725 A1     5/2012
WO     WO2013/184213 A2 * 12/2013 ............. A61B 6/484

OTHER PUBLICATIONS

International Search Report and Written Opinioin under date of mailing of Jan. 10, 2014 in connection with PCT/US2013/031602.

*Primary Examiner* — Allen C. Ho
(74) *Attorney, Agent, or Firm* — Quarles & Brady LLP

(57) ABSTRACT

Described here is a method for performing phase contrast imaging using an array of independently controllable x-ray sources. The array of x-ray sources can be controlled to produce a distinct spatial pattern of x-ray radiation and thus can be used to encode phase contrast signals without the
(Continued)

need for a coded aperture. The lack of coded aperture increases the flexibility of the imaging method. For instance, because a fixed, coded aperture is not required, the angular resolution of the imaging technique can be increased as compared to coded-aperture imaging. Moreover, the lack of a radioopaque coded aperture increases the photon flux that reaches the subject, thereby increasing the attainable signal-to-noise ratio.

10 Claims, 2 Drawing Sheets

(51) Int. Cl.
   *G01V 5/00* (2006.01)
   *H01J 35/06* (2006.01)
   *H01J 35/12* (2006.01)
(52) U.S. Cl.
   CPC ........... *A61B 6/4405* (2013.01); *G01N 23/04* (2013.01); *G01V 5/0016* (2013.01); *G01V 5/0041* (2013.01); *H01J 35/065* (2013.01); *H01J 35/12* (2013.01); *G21K 2207/005* (2013.01); *H01J 2201/30449* (2013.01); *H01J 2235/062* (2013.01); *H01J 2235/068* (2013.01); *H01J 2235/087* (2013.01); *H01J 2235/186* (2013.01)
(58) Field of Classification Search
   USPC .................................................. 378/2, 36, 62
   See application file for complete search history.

(56) References Cited

U.S. PATENT DOCUMENTS

| | | | | | |
|---|---|---|---|---|---|
| 4,246,483 | A * | 1/1981 | Weiss | ...................... | A61B 6/025 378/193 |
| 4,322,808 | A * | 3/1982 | Weiss | ...................... | A61B 6/025 378/2 |
| 4,630,296 | A * | 12/1986 | Haaker | ................. | G06T 11/006 378/2 |
| 5,606,165 | A * | 2/1997 | Chiou | ...................... | G01T 1/167 250/363.06 |
| 5,757,005 | A * | 5/1998 | Callas | ................... | G01T 1/2928 250/363.06 |
| 5,930,314 | A * | 7/1999 | Lanza | ................... | G01N 23/204 250/358.1 |
| 6,195,412 | B1 * | 2/2001 | Tobin, Jr. | ................ | G01T 1/295 250/363.03 |
| 6,333,968 | B1 * | 12/2001 | Whitlock | ............... | B82Y 10/00 378/122 |
| 6,392,235 | B1 * | 5/2002 | Barrett | .................. | G01T 1/295 250/363.06 |
| 6,594,335 | B2 * | 7/2003 | Davidson | ............... | A61B 6/484 378/119 |
| 6,674,837 | B1 * | 1/2004 | Taskar | .................... | A61B 6/00 378/122 |
| 6,737,652 | B2 * | 5/2004 | Lanza | ................... | G01T 1/295 250/237 R |
| 6,950,495 | B2 * | 9/2005 | Nelson | ................... | G01T 1/295 378/156 |
| 7,082,182 | B2 * | 7/2006 | Zhou | ...................... | A61B 6/032 378/10 |
| 7,103,138 | B2 * | 9/2006 | Pelc | ...................... | A61B 6/032 378/4 |
| 7,192,031 | B2 * | 3/2007 | Dunham | ............... | A61B 6/032 378/122 |
| 7,295,651 | B2 * | 11/2007 | Delgado | ............. | G01N 23/046 378/10 |
| 7,330,533 | B2 * | 2/2008 | Sampayon | .............. | H01J 35/30 378/119 |
| 7,463,712 | B2 * | 12/2008 | Zhu | ...................... | A61B 6/5282 378/2 |
| 7,476,863 | B2 * | 1/2009 | Lamadie | ................. | G01T 1/295 250/237 R |
| 7,623,614 | B2 * | 11/2009 | Shefsky | ................. | G01N 23/02 378/2 |
| 7,791,033 | B2 * | 9/2010 | Danielsson | ........... | G01T 1/1648 250/370.01 |
| 7,809,114 | B2 * | 10/2010 | Zou | ...................... | H01J 1/3048 378/122 |
| 7,826,594 | B2 * | 11/2010 | Zou | ........................... | H01J 1/30 378/10 |
| 7,864,917 | B2 * | 1/2011 | Ribbing | ................. | A61B 6/032 378/10 |
| 7,920,673 | B2 * | 4/2011 | Lanza | .................... | G02B 27/52 378/62 |
| 7,940,888 | B2 * | 5/2011 | Tsujii | ..................... | A61B 6/4007 378/21 |
| 7,978,816 | B2 * | 7/2011 | Matsuura | ............... | A61B 6/032 378/62 |
| 7,991,114 | B2 * | 8/2011 | Okunuki | ................. | A61B 6/032 378/122 |
| 7,991,120 | B2 * | 8/2011 | Okunuki | ................. | A61B 6/00 378/122 |
| 8,129,686 | B2 * | 3/2012 | Zelakiewicz | ........... | G01T 1/295 250/363.06 |
| 8,237,124 | B2 * | 8/2012 | Marwala | ................ | A61B 6/583 250/363.06 |
| 8,243,879 | B2 * | 8/2012 | Itoh | ........................ | G21K 1/025 359/238 |
| 8,304,737 | B2 * | 11/2012 | Tobin, Jr. | ................ | G01T 1/295 250/363.06 |
| 8,326,054 | B2 * | 12/2012 | Chen | ...................... | A61B 6/032 378/4 |
| 8,340,246 | B2 * | 12/2012 | Kang | ....................... | A61B 6/06 378/146 |
| 8,503,614 | B2 * | 8/2013 | Legagneux | ........... | H01J 35/065 378/122 |
| 8,509,387 | B2 * | 8/2013 | Tsujii | ...................... | A61B 6/06 378/122 |
| 8,855,265 | B2 * | 10/2014 | Engel | ...................... | A61B 6/00 378/36 |
| 8,861,686 | B2 * | 10/2014 | Kim | ....................... | G03B 42/02 378/149 |
| 9,008,268 | B2 * | 4/2015 | Okunuki | ................. | A61B 6/032 378/122 |
| 9,164,045 | B2 * | 10/2015 | Munro | ................ | G01N 23/046 |
| 9,335,281 | B2 * | 5/2016 | Marks | .................. | G01N 23/201 |
| 9,344,700 | B2 * | 5/2016 | Zalevsky | ............. | G02B 26/06 |
| 9,347,893 | B2 * | 5/2016 | Nelson | ............... | G01N 23/04 |
| 9,439,615 | B2 * | 9/2016 | Stampanoni | ........... | A61B 6/484 |
| 9,445,775 | B2 * | 9/2016 | Das | ..................... | A61B 6/484 |
| 9,575,015 | B2 * | 2/2017 | Sung | ............... | G01N 23/20075 |
| 9,700,275 | B2 * | 7/2017 | Stampanoni | ........... | A61B 6/483 |
| 9,916,655 | B2 * | 3/2018 | Stampanoni | .......... | G06T 7/0012 |
| 2001/0038680 | A1 | 11/2001 | Davidson | | |
| 2010/0246764 | A1 | 9/2010 | Itoh et al. | | |

\* cited by examiner

METHOD FOR CODED-SOURCE PHASE CONTRAST X-RAY IMAGING

CROSS-REFERENCE TO RELATED APPLICATIONS

This application represents the national stage entry of PCT International Application No. PCT/US2013/031602 filed Mar. 14, 2013, which claims the benefit of U.S. provisional Patent Application 61/646,577, filed on May 14, 2012 both of which are incorporated herein by reference for all purposes.

STATEMENT REGARDING FEDERALLY SPONSORED RESEARCH

This invention was made with government support under N666001-11-4204 awarded by the Defense Advanced Research Projects Agency. The government has certain rights in the invention.

BACKGROUND OF THE INVENTION

The field of the invention is systems and methods for x-ray phase contrast imaging. More particularly, the invention relates to systems and methods for x-ray phase contrast imaging using a coded-source imaging technique.

Coded aperture imaging has been proposed in the past as a means for improving the spatial resolution, sensitivity, and signal-to-noise ratio ("SNR") of images formed by x-ray radiation. For many imaging applications, coded aperture cameras have proven advantageous relative to other candidate systems, including the single pinhole camera and multi-hole collimator systems. In contrast to these other systems, for instance, the coded aperture camera is characterized by high sensitivity, while simultaneously achieving exceptional spatial resolution in the reconstructed image.

In contrast to the single pinhole camera, coded aperture systems utilize multiple, specially-arranged pinholes to increase the overall photon transmission, and hence the sensitivity, of the imaging camera. In operation, radiation from the object to be imaged is projected through the coded aperture mask and onto a position-sensitive detector. The coded aperture mask contains a number of discrete, specially arranged elements that are either opaque or transparent to the incident photons. The raw signal from the detector does not reflect a directly recognizable image, but instead represents the signal from the object that has been modulated or encoded by the particular aperture pattern. This recorded signal can then be digitally or optically processed to extract a reconstructed image of the object.

Coded-aperture imaging has its drawbacks, however, in that the improvement in imaging performance provided by the method depends on the nature of the object being imaged. Due to this, and counter-intuitively, the actual SNR improvement attainable with coded-aperture imaging may be better for aperture patterns that have a smaller fraction of open area despite the smaller fraction of available x-rays that are used. Because the imaging technique requires the use of one or more coded apertures that are radioopaque, many photons that could otherwise be used to for imaging are left unused. This, in turn, lowers the potential SNR that can be achieved with coded aperture imaging, but as mentioned above, this depends on the nature of the object being imaged. Additionally, the coded aperture places limits on the field-of-view and angular resolution that can be realized. For instance, the angular resolution of the coded aperture imaging system is fixed by the aperture separation from the detector plane, the configuration of the detector array, and the aperture pattern. Coded aperture imaging systems are also limited in that they require fixed apertures and thus can only vary their detection gaze by physically adjusting the relative positions of the x-ray source, aperture, subject, and/or detector.

It would therefore be desirable to provide a method for phase contrast imaging that can utilize the advantages of coded-source imaging while improving on the limitations of currently available coded-aperture imaging techniques, including the reliance on a fixed, coded aperture that can lower attainable SNR and limit angular resolution.

SUMMARY OF THE INVENTION

The present invention overcomes the aforementioned drawbacks by providing a method for x-ray phase contrast imaging using a coded x-ray source.

It is an aspect of the invention to provide a method for phase contrast imaging using an array of independently controllable x-ray sources. The method includes directing an array of independently controllable x-ray sources to produce x-ray radiation in a distinct spatial pattern by selectively energizing x-ray sources in the array. Phase-contrast signals of the x-ray radiation are then detected using an x-ray detector after the x-ray radiation passes through a subject. An image of the subject is then reconstructed by performing a compressed sensing reconstruction technique on the detected phase-contrast signals. This reconstructed image depicts an image contrast indicative of phase shifts in the x-ray radiation.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
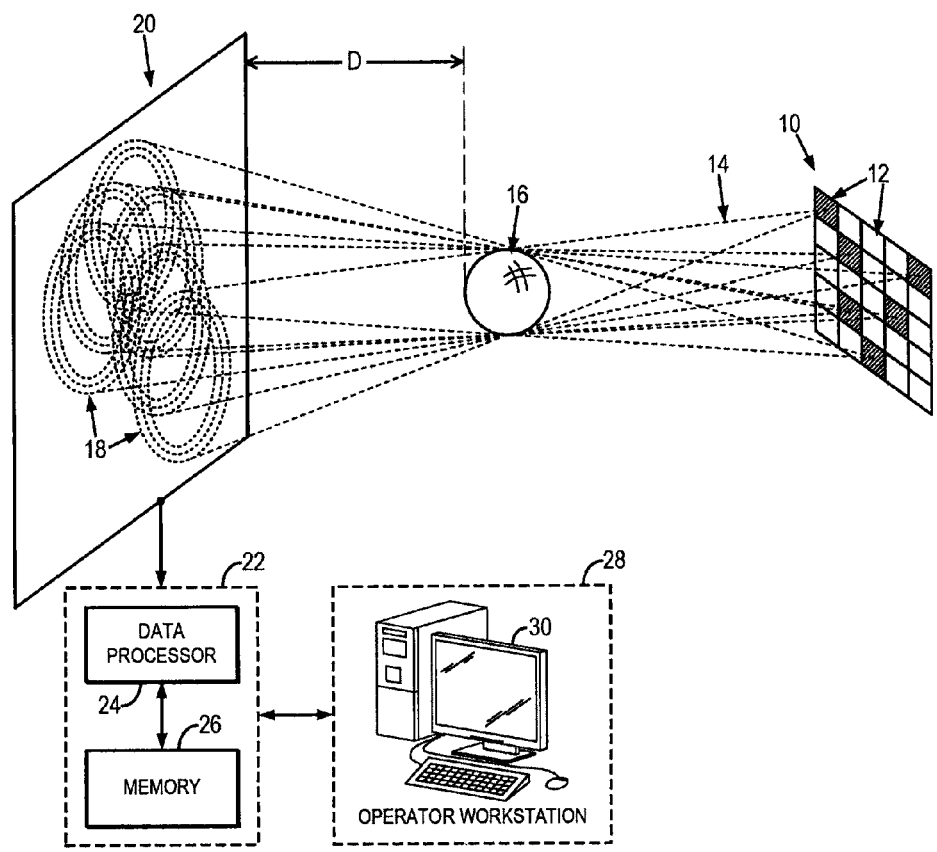
FIG. 1 illustrates phase contrast imaging using an array of independently controllable x-ray sources without requiring a coded aperture.

Described here is a method for performing phase contrast imaging using a coded micro-focus array of x-ray sources. Because the x-ray source itself is coded, this method of imaging does not require the use of the coded aperture required in currently available coded-aperture imaging techniques. The lack of coded aperture increases the flexibility of the imaging method. For instance, because a fixed, coded aperture is not required, the angular resolution of the imaging technique can be increased as compared to coded-aperture imaging. Moreover, the lack of a radioopaque coded aperture increases the photon flux that reaches the subject, thereby increasing the SNR attainable with the method of the present invention.

In coded-aperture imaging, sensitivity is improved by having many pinholes that each individually have relatively low sensitivity. In a similar vein, the present invention uses a coded-source composed of many individually weak x-ray sources that, when combined, produce the equivalent of a relatively strong source. For phase contrast imaging, a small spot size is required; however, this requirement is inconsistent with high power because of tube heating. The present invention overcomes this limitation by cleverly combining the signals from many small sources to produce a single phase coherent image.

In the case of coded-aperture imaging, the relatively low sensitivity of a single pinhole is improved by the use of N pinholes, often as many as several thousand. The individual pinholes form images on the recording device that overlap; however, if the pinhole pattern is suitably coded, the recorded pattern can be decoded to form an image with SNR that is enhanced by as much as $\sqrt{N}$ better than a single pinhole.

In the case of phase contrast imaging, one common approach uses a relatively small x-ray source, such as a source that is ten μm or less in diameter, to provide a coherent source of x-rays and to produce a phase contrast image. It is well known, however, that x-ray sources using small diameters are limited in x-ray power before damage occurs to the x-ray tube anode. By analogy to the coded aperture, a coded source includes N sources, each of which produce a phase contrast image. By suitably encoding the source positions, a similar decoding can be done and the result is an improvement in SNR by as much as $\sqrt{N}$ while avoiding damage to the anode. It can be shown that decoding approaches used for coded apertures can also be used for coded sources.

The basic principles of x-ray image formation in radiography, tomography, and inspection rely on differences the attenuation properties of materials as the source of image contrast. Phase contrast imaging, however, uses the wave nature of x-rays to form images based on small differences in the x-ray refractive index of materials. As a result, images may be formed even for materials that cannot easily be imaged or distinguished using conventional absorption-based x-ray imaging because they have very similar attenuation properties. Images for such materials can nevertheless be formed via phase contrast imaging because materials often have different phase-shift properties, which can be imaged using phase contrast imaging methods.

The behavior of x-rays as they travel through a sample can be described using a complex index of refraction, as in conventional optics. In the x-ray region, the index of refraction, n (where n represents the speed of the x-rays in the medium over the speed of the x-rays in a vacuum), deviates only slightly from unity. The index of refraction can be expressed as, $$n = 1 - \delta - i\beta \qquad (1);$$

where β described the absorption of x-rays and the phase-shift term, δ, incorporates refractive effects. X-rays passing through regions of differing δ pick up different relative phases, which correspond to refraction of the x-rays, and produce a distorted wave front. These phase differences can then be detected by various phase-contrast techniques. Advantageously, because phase contrast imaging relies only on the refraction of x-rays to produce image contrast, and not the absorption of those x-rays, imaging can be conducted at higher energies with a reduced dose of absorbed radiation being imparted to the patient. For example, dose can be reduced by a factor of twenty-five or more, thereby reducing potential damage to tissues.

In general, there are three categories of phase contrast imaging. These include interferometry, diffractometry, and in-line holography. Defining the phase change introduced in incident x-rays passing through the subject by integrating over the ray path as follows, $$\phi = -\frac{2\pi}{\lambda} \int \delta(s) ds; \qquad (2)$$

where λ is the wavelength of x-rays. With this definition, the aforementioned categories of phase contrast imaging can be viewed as recording measurements of $\varphi$, $\nabla\varphi$, and $\nabla^2\varphi$, respectively.

In-line holography methods implement one or more pinhole sources that are spatially coherent and act as sources for a spherical wave. Each spherical wave interferes with waves that have been refracted (e.g., phase shifted) by the object being imaged. This interference results in an enhancement of the edges even though the absorption difference may be very slight, as is often the case for biological tissues or materials such as composites or polymers.

In order to have a spatially coherent source, either a very small bright x-ray source, such as that from a synchrotron, or a pinhole source can be used to establish spatial coherence. In the method of the present invention, an array of micro-focus x-ray sources can be used to generate spatially coherent x-rays.

An array of micro-focus x-ray sources can be configured to operate as a coded source for x-ray phase contrast imaging. In general, the coded source is composed of a plurality of independently controllable micro-focus x-ray sources. Preferably, these x-ray sources are each capable of producing a focal spot size less than 20 μm, such as between 7 and 20 μm. Free-space propagation techniques, where the image is taken at a specified distance sufficient to allow the various components of the transmitted x-ray radiation waves to interfere freely, can then be used for phase retrieval.

Referring to FIG. 1, an array 10 of independently controllable x-ray sources 12, such as an array of micro-focus x-ray sources, is provided and used to produce a distinct spatial pattern of x-ray radiation 14 by selectively energizing x-ray sources 12 in the array 10. As a result, x-ray radiation 14 passing through the subject 16 being imaged produces images 18 of the subject 16 that are projected onto a detector array 20. The detector array 20 can be any suitable array of x-ray detectors, including amorphous silicon digital x-ray detectors with either Gadox (gadolinium oxysulphide) or cesium iodide (CsI) (Tl) scintillators with an expected resolution of around 100-200 μm. Alternatively the detector array 20 can be a photostimulable phosphor plate (also known as an imaging plate). Such a plate provides digital images with a resolution up to 25 μm and uses a plate reader to detect the measured phase contrast signal data. The separation distance, D, between the subject 16 and the detector array 20 is preferably larger than about one meter; however, shorter separation distances can also be used. When shorter distances are used, a dispersive element may be advantageously used. To help disperse the x-ray radiation 14 before it impinges on the detector array 20. Additionally, the effective detector pitch of the detector array 20 is preferable less than about 10 μm. This requires a very high spatial resolution, which can be achieved using compressed sensing reconstruction techniques.

The array 10 of x-ray sources 12 each cast a particular image 18 on the detector array 20, thereby superimposing many individual patterns on the detector plane. At the points of overlap between the images 18, the resulting image can include the product of interference due to a phase shift in the x-ray radiation 14 from each x-ray source 12 as a function of its passage through the subject 16. The detector array 20 thus provides detection of phase contrast signals that are representative of the energy and pattern of the transmitted x-ray radiation 14.

A data processor 22, which can be a programmable computer, is coupled, physically or wirelessly, with the detector array 20 and receives signals from the detector array 20 corresponding to the detected phase contrast signals and the spatial distribution of the signals in the plane of the detector array 20. The data processor 22 includes a processor 24 coupled with computer-readable memory 26, on which is stored software code for characterizing the subject 16, including reconstructing an image of the subject 16 or components within the subject 16, based upon the transmitted x-ray radiation 14 and the configuration of the coded spatial pattern of x-ray radiation 14 produced by the array 10 of x-ray sources 12. The data processor 22 can also be coupled with an operator workstation 28 that can include an electronic display 30 for viewing images reconstructed by the data processor 22. The operator workstation 28 can be programmed to generate and send commands to the data processor 22 in order to record phase contrast signals from the detector array 20 and to reconstruct images of the subject 16 therefrom.

Figure 2:
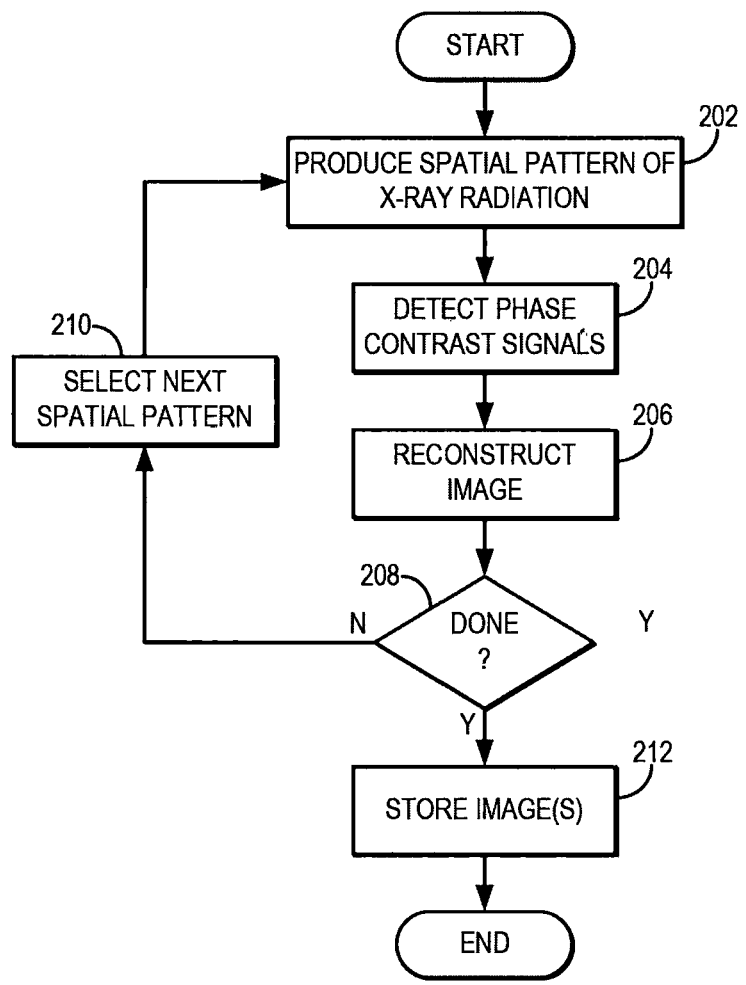
FIG. 2 is a flowchart setting forth the steps of an example of a method for phase contrast imaging using an array of independently controllable x-ray sources without requiring a coded aperture.

Referring now to FIG. 2, a flowchart setting forth the steps of an example of a method for phase contrast imaging using a coded x-ray source is illustrated. The method begins by producing a distinct spatial pattern of x-ray radiation that impinges on the subject to be imaged using an array of independently controllable x-ray sources, as indicated at step 202. Notably, the imaging method does not require the use of a fixed or adaptive coded aperture to achieve encoding of the acquired data; instead, the array of independently controllable x-ray sources is used to generate the distinct pattern of x-ray radiation, similar to the multiple pinholes of x-ray radiation produced when using a conventional x-ray source and a coded aperture.

Figure 3:
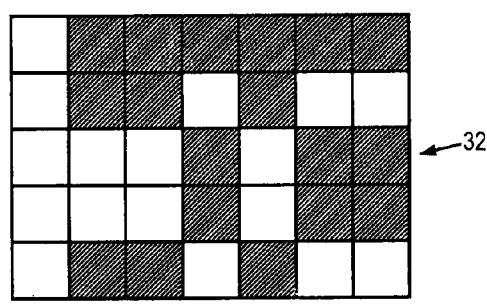
FIG. 3 is an example of a spatial pattern of excitation to be provided to an array of independently controllable x-ray sources.

The focal spot size of an x-ray source is preferably less than 20 μm. For example, the focal spot size may be in the range of 7-20 μm. Using such a small focal spot results in a small photon flux per x-ray source; however, by using an array 10 of x-ray sources 12 and proper spatial encoding, such an array 10 of x-ray sources 12 can be used to produce quality phase contrast images of the subject 16. Thus, the method of the present invention includes directing an array 10 of independently controllable x-ray sources 12, such as micro-focus x-ray sources, to produce a distinct spatial pattern of x-ray radiation 14 that impinges on the subject 16 being images. The distinct spatial patterns can be generated by selectively energizing x-ray sources 12 in the array 10. By way of example, the distinct spatial patterns can be selected as a uniformly redundant array ("URA"), a modified URA ("MURA"), a random array, and an approximation of a Fresnel zone plate or fractal zone plate pattern. Methods for generating URAs are described by A. Busboom, et al., in "Uniformly Redundant Arrays," *Experimental Astronomy*, 1998; 8:97-123. For example, a perfect binary array method can be used to determine a pattern of which x-ray sources 12 to energize in the array 10 of x-ray sources 12. An example of a spatial pattern 32 is illustrated in FIG. 3, in which the spatial pattern is a URA pattern.

The distinct spatial pattern of x-ray radiation 14 then travels through the subject 16. While travelling through the subject 16, the phase of each independent x-ray beam is modified by the internal environment of the subject 16, as described above. The x-ray radiation 14 that exit the subject 16 and impinge on an a detector array 20 thus indicate a phase contrast. These phase contrast signals are detected by the detector array 20, as indicated at step 204. From the detected phase contrast signals, an image can be reconstructed, as indicated at step 206. In general, a compressed sensing method can be used to reconstruct the image from the phase contrast signals. An example of a compressed sensing method includes seeking a target image, X, that minimizes the $l_1$-norm of a sparse representation of the target image among all images that are consistent with the physical measurements. Stated mathematically, this reconstruction process can be posed as the following minimization problem, $$\min_{X} \|\Psi X\|_1 \text{ such that } AX = Y; \quad (1)$$

where $\Psi$ is a sparsifying transform; X is the target image of the subject 16 reordered as a vector; A is a system matrix that describes the x-ray measurements; and Y is the measured phase contrast signals. By way of example, the discrete gradient transform can be used as the sparsifying transform, $\Psi$. As a result, Eqn. (1) reduces to the standard total variation ("TV") norm, which is given by, $$\|\Psi X\|_1 = TV(X) = \sum_{m,n} \sqrt{(X_{m+1,n} - X_{m,n})^2 + (X_{n+1} - X_{m,n})^2}. \quad (2)$$

A determination is then made as to whether additional images of the subject are desired, as indicated at step 208. If more images are desired, the spatial pattern of the array 10 of x-ray sources 12 can be changed, as indicated at step 210, before repeating steps 202-206. When all of the desired images have been obtained, the images are stored for later processing or viewing, as indicated at step 212.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for phase contrast imaging using an array of independently controllable x-ray sources, the steps of the method comprising:
    a) directing an array of independently controllable x-ray sources to produce x-ray radiation in a distinct spatial pattern by selectively energizing the independently controllable x-ray sources in the array;
    b) detecting phase-contrast signals of the x-ray radiation after the x-ray radiation passes through a subject using an x-ray detector; and
    c) reconstructing an image of the subject by performing a compressed sensing reconstruction technique on the detected phase-contrast signals, wherein the reconstructed image depicts an image contrast indicative of phase shifts in the x-ray radiation.

2. The method as recited in claim 1, in which each x-ray source of the array of independently controllable x-ray sources has a focal spot sized less than twenty micrometers.

3. The method as recited in claim 1, in which the x-ray detector is separated from the subject by at least one meter.

4. The method as recited in claim 1, in which the x-ray detector has an effective detector pitch of less than ten micrometers.

5. The method as recited in claim 1, in which the distinct spatial pattern is selected as at least one of a uniformly redundant array (URA) and a modified uniformly redundant array (MURA).

6. The method as recited in claim 1, in which step c) includes determining a target image, X, that minimizes an objective function defined as, $\|\Psi X\|_1$; wherein $\Psi$ is a sparsifying transform that transforms the target image, X, into a sparse domain.

7. The method as recited in claim 6, in which the sparsifying transform is a discrete gradient transform.

8. The method as recited in claim 1, in which the subject is at least one of a human and an animal.

9. The method as recited in claim 1, in which the subject is at least one of a piece of luggage and a cargo container.

10. The method as recited in claim 9, in which the at least one of a piece of luggage and a cargo container includes an explosive, and the method further comprises identifying the explosive by analyzing the image reconstructed in step c).

* * * * *

UNITED STATES PATENT AND TRADEMARK OFFICE
CERTIFICATE OF CORRECTION

Page 1 of 1

PATENT NO. : 10,045,752 B2
APPLICATION NO. : 14/400703
DATED : August 14, 2018
INVENTOR(S) : Rajiv Gupta et al.

It is certified that error appears in the above-identified patent and that said Letters Patent is hereby corrected as shown below:

In the Specification

Column 5, Line 21, "subject 16" should be --subject--.

Column 5, Line 37, "radiation that" should be --radiation 14 that--.

Column 5, Line 38, "subject to" should be --subject 16 to--.

Column 5, Line 38, "array of" should be --array 10 of--.

Column 5, Line 39, "sources," should be --sources 12,--.

Column 5, Line 42, "array of" should be --array 10 of--.

Column 5, Line 43, "sources is" should be --sources 12 is--.

Column 5, Line 44, "radiation," should be --radiation 14--.

Column 5, Line 51, "array 10" should be --x-ray 10--.

Column 5, Line 52, "array 10" should be --x-ray 10--.

In the Claims

Column 7, Claim 2, Line 3, "than twenty" should be --than about twenty--.

Column 7, Claim 3, Line 5, "least one" should be --least about one--.

Signed and Sealed this
Twenty-fifth Day of September, 2018

Andrei Iancu
*Director of the United States Patent and Trademark Office*